US005583031A

United States Patent [19]
Stern

[11] Patent Number: 5,583,031
[45] Date of Patent: Dec. 10, 1996

[54] EMPTY MAJOR HISTOCOMPATIBILITY CLASS II HETERODIMERS

[75] Inventor: Lawrence J. Stern, Arlington, Mass.

[73] Assignee: President and Fellows of Harvard College, Cambridge, Mass.

[21] Appl. No.: 831,895

[22] Filed: Feb. 6, 1992

[51] Int. Cl.$^6$ .............................. C12N 5/06; C12N 5/10; C07K 14/74

[52] U.S. Cl. ................ 435/240.2; 435/69.3; 435/320.1; 530/395; 530/403; 530/868; 424/184.1; 424/185.1; 424/193.1; 514/8

[58] Field of Search ................................. 424/88, 184.1, 424/278.1, 185.1, 193.1; 514/2, 8; 530/395, 402, 403, 868; 435/320.1, 252.3, 69.1, 69.3, 70.3, 69.6, 240.2

[56] References Cited

U.S. PATENT DOCUMENTS

| | | | |
|---|---|---|---|
| 4,478,823 | 10/1984 | Sanderson | 424/88 |
| 4,816,397 | 3/1989 | Boss et al. | 435/68 |
| 5,130,297 | 7/1992 | Sharma et al. | 514/8 |
| 5,260,442 | 11/1993 | Clark et al. | 530/403 |
| 5,314,813 | 5/1994 | Peterson et al. | 435/172.3 |

FOREIGN PATENT DOCUMENTS

PCT/US93/01006  3/1993  WIPO.

OTHER PUBLICATIONS

Marguiles, D. H. et al. Immunol Res. 6;101–116(1987). "Engineering Soluble, Major Histocompatibility molecules: why and how."
Robinson, M. A. et al in *Fundamental Immunology* (W F Paul, ed.)(1989), "MHC Antigens and Genes". pp. 488–539.
Stern, L. J., et al, Cell 68:465–477 (Feb. 1992) "The human class II MHC protein HLA–DR1 assembles as empty a B heterodimers in the absence of antigenic peptide".
Paul, W. F. (ed), *Fundamental Immunology* (1989), pp. 70–72.
Germain, R. N., et al. Nature 353:134–139 (12 Sep. 1991), "MHC Class II structure, occupancy and surface expression determined by post–endoplasmic antigen binding".
Jackson, M. R., et al., P.N.A.S. (USA) 89:12117–12121 (Dec., 1992), "Empty and peptide–containing conformers of class I major histocompatitiblity complex molecules expressed in Drosophila melanogaster cells".
Luckow, V. A., et al., Virology 170:31–39 (1989), "High level epxression of nofused foreign genes with *Autographa californica* nuclear polyhedrosis virus expression vectors".
Peterson, M., et al., Nature 345:172–174 (10 May 1990), "Invariant chain influences the immunological recognition of MHC class II molecules".
Stern, L., et al., Cell 68:465–477 (Feb. 7, 1992), "The human class II MHC protein HLA–DR1 assembles as empty alpha-beta heterodimers in the absence fo antigenic peptide".
Traunecker, A., et al., Nature 331:84–86 (7 Jan. 1988), "Soluble CD4 molecules neutralize human immunodeficiency virus type 1".

Rose et al., Cell, vol. 30, Oct. 1982, pp. 753–762.
Luckow et al., Bio/Technology, vol. 6, issued Jan. 1988, pp. 47–55.
Long et al., Human Immunology, vol. 31(4), Issued Aug. 1991, pp. 229–235.
Wiman et al., Proc. Natl. Acad. Sci, USA, vol. 79, pp. 1703–1707, Mar. 1982.
Wake et al., Proc. Natl. Acad. Sci, USA, vol. 79, pp. 6979–6983, Nov. 1982.
Kvist et al., Cell, vol. 29, pp. 61–69, May 1982.
Sharma et al., Proc. Natl. Acad. Sci. USA, 88:11465–11469, 1991.
Rudensky et al., Nature 353:622–627, 1991.
Davidson et al., Cell 67:105–116, 1991.
Germain et al. Nature 353:134–139, 1991.
Tampe et al., Proc. Natl. Acad. Sci. USA, 88:4661–4665, 1991.
Falk et al., Nature 351:290–296, 1991.
Ortiz–Navarrete et al., Proc. Natl. Acad. Sci. USA 88:3594–3597, 1991.
Wettstein et al., J. Exp. Med. 174:219–228, 1991.
De Bruijn et al., Eur. J. Immunol. 21:2963–2970, 1991.
Gorga et al., Res. Immunol. 142:401–407, 1991.
Rothbard et al., Annu. Rev. Immunol. 9:527–565, 1991.
Jardetzky et al., Nature 353:326–329, 1991.
Van Bleek et al., Nature 348:213–216, 1990.
O'Sullivan et al., J. Immunol. 145:1799–1808, 1990.
Ljunggren et al., Nature 346:476–480, 1990.
Townsend et al., Cell 62:285–295, 1990.
Yewdell et al., Cell 62:203–206, 1990.
Harding et al., Proc. Natl. Acad. Sci. USA 87:5553–5557, 1990.
Neefjes et al., Cell 61:171–183, 1990.
Roche et al., The Journal of Immunology 144:1849–1856, 1990.
Guagliardi et al., Nature 343:133–139, 1990.
Jardetzky et al., EMBOJ. 9:1797–1803, 1990.
Busch et al., Journal of Immunological Methods, 134:1–22, 1990.
Townsend et al., Nature 340:443–448, 1989.
Ceppellini et al., Nature 339:392–394, 1989.
Nuchtern et al., Nature 339:223–226, 1989.
Luckow et al., Virology 170:31–39, 1989.
Chen et al., Nature 337:743–745, 1989.
Traunecker et al., Immunology Today 10:29–32, 1989.
Buus et al., Science 242:1045–1047, 1988.
Bjorkman et al., Nature 329:506–512, 1987.

(List continued on next page.)

*Primary Examiner*—Kay K. A. Kim
*Assistant Examiner*—Thomas Cunningham
*Attorney, Agent, or Firm*—Fish & Richardson P.C.

[57] ABSTRACT

The invention features an isolated sample of mammalian class II major histocompatibility heterodimers which are membrane-associated or in soluble form, and which are capable of binding added antigenic peptide; methods for producing large amounts of the soluble or membrane-associated histocompatibility protein by expression of DNA encoding the α and β polypeptides; and methods for loading these heterodimers with any desired antigen.

18 Claims, 6 Drawing Sheets

OTHER PUBLICATIONS

Quill et al., The Journal of Immunology 138:3704–3712, 1987.

Buus et al., Immunological Reviews 115–141, 1987.

Gorga et al., The Journal of Biological Chemistry 262:16087–16094, 1987.

Matsudaira, The Journal of Biological Chemistry 262:10035–10038, 1987.

Watts et al., Proc. Natl. Acad. Sci. USA 83:9660–9664, 1986.

Gorga et al., Cellular Immunology 103:160–173, 1986.

Buus et al., Cell 47:1071–1077, 1986.

Blake et al., Analytical Biochemistry 136:175–179, 1984.

Shackelford et al., The Journal of Immunology 130:274–282, 1983.

Lampson et al., The Journal of Immunology 125:293–299, 1980.

Laemmli, Nature 227:680–685, 1970.

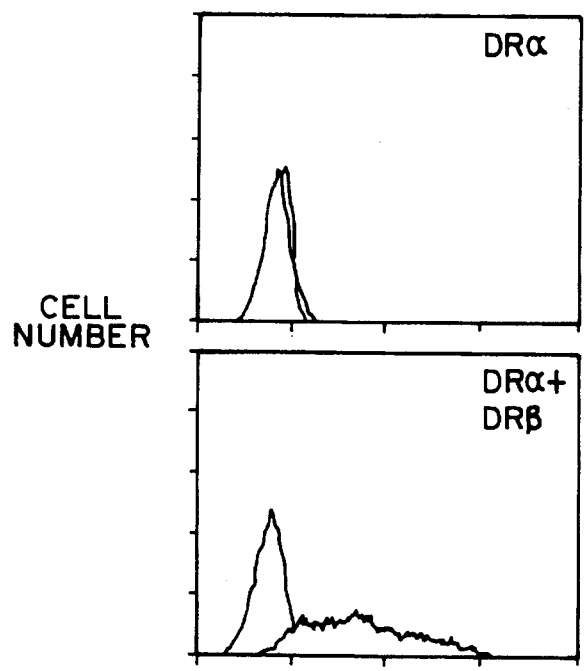
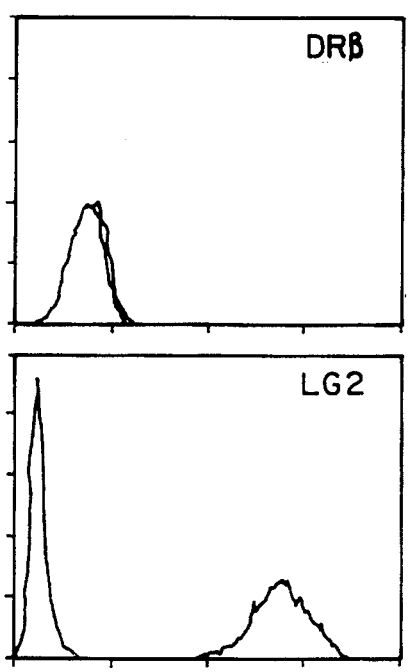
FIG. 2A, FIG. 2B, FIG. 2C, FIG. 2D
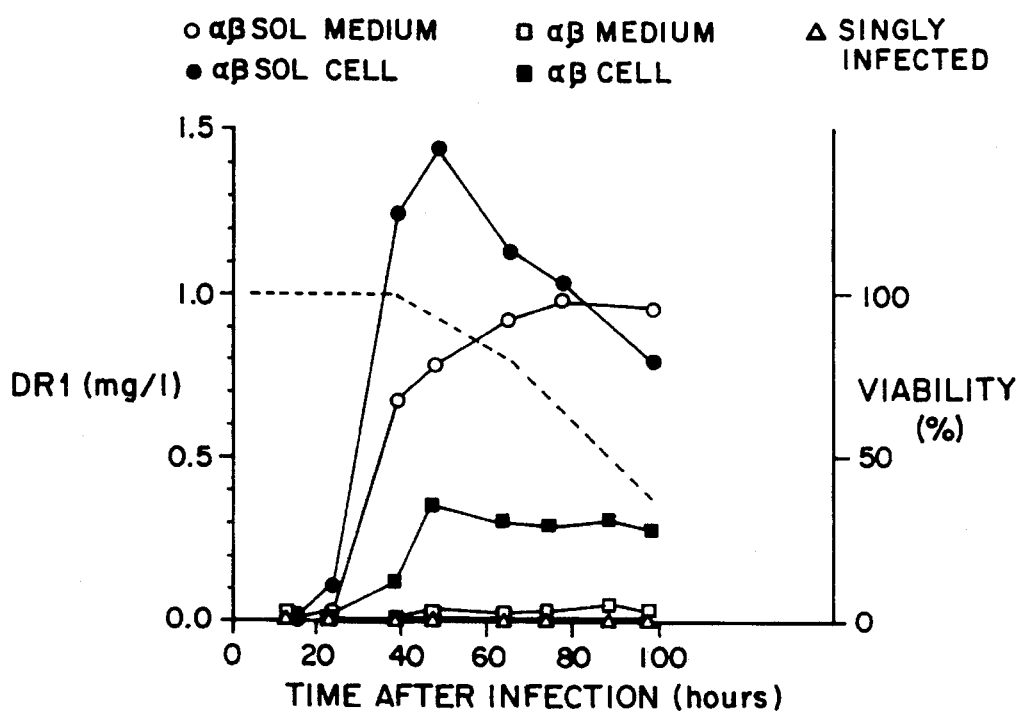
FIG. 3

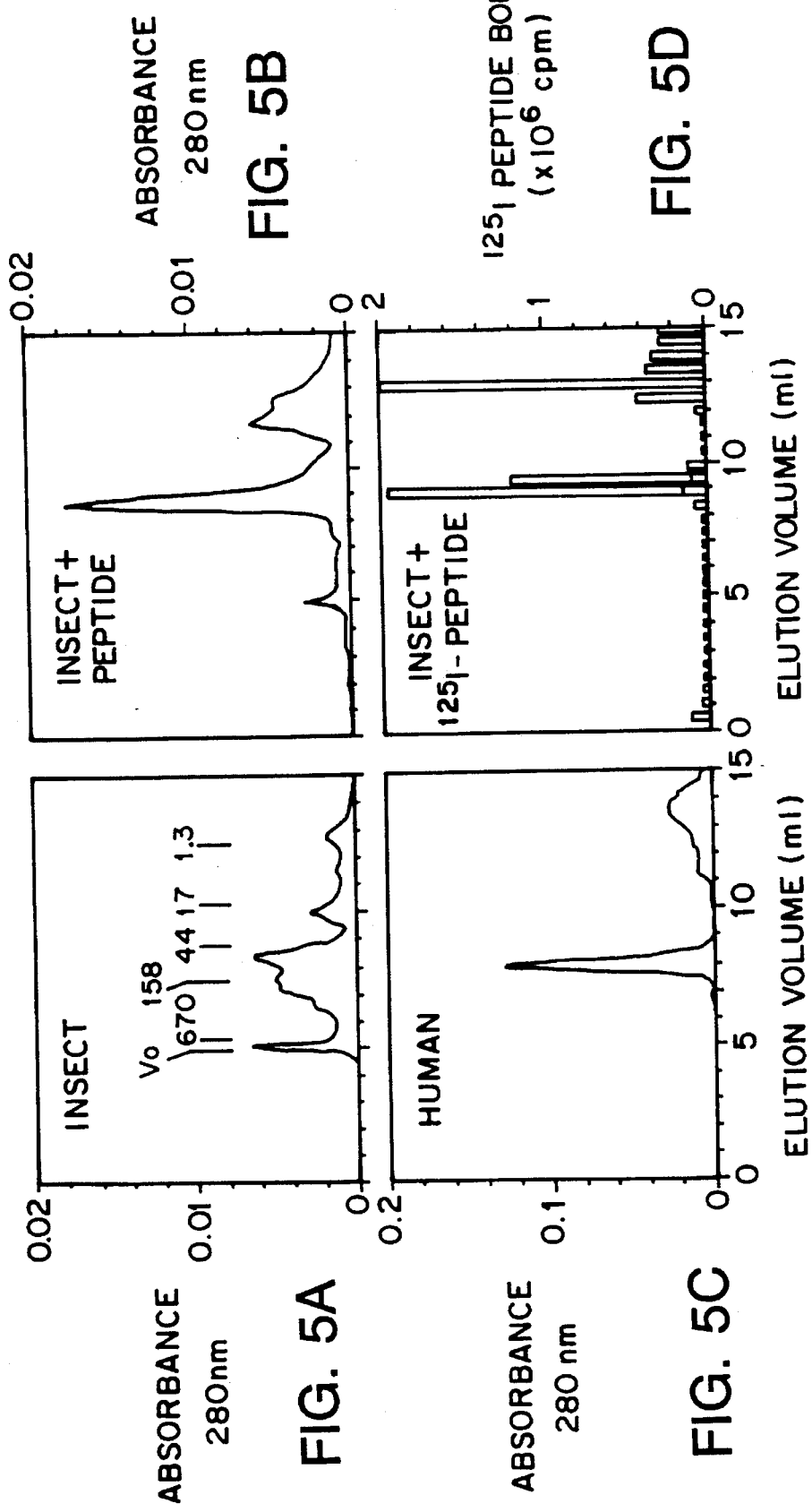

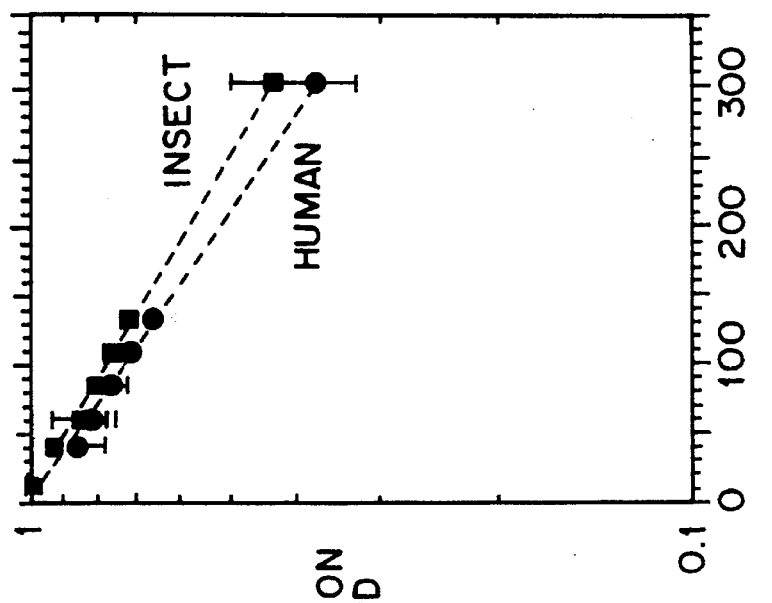
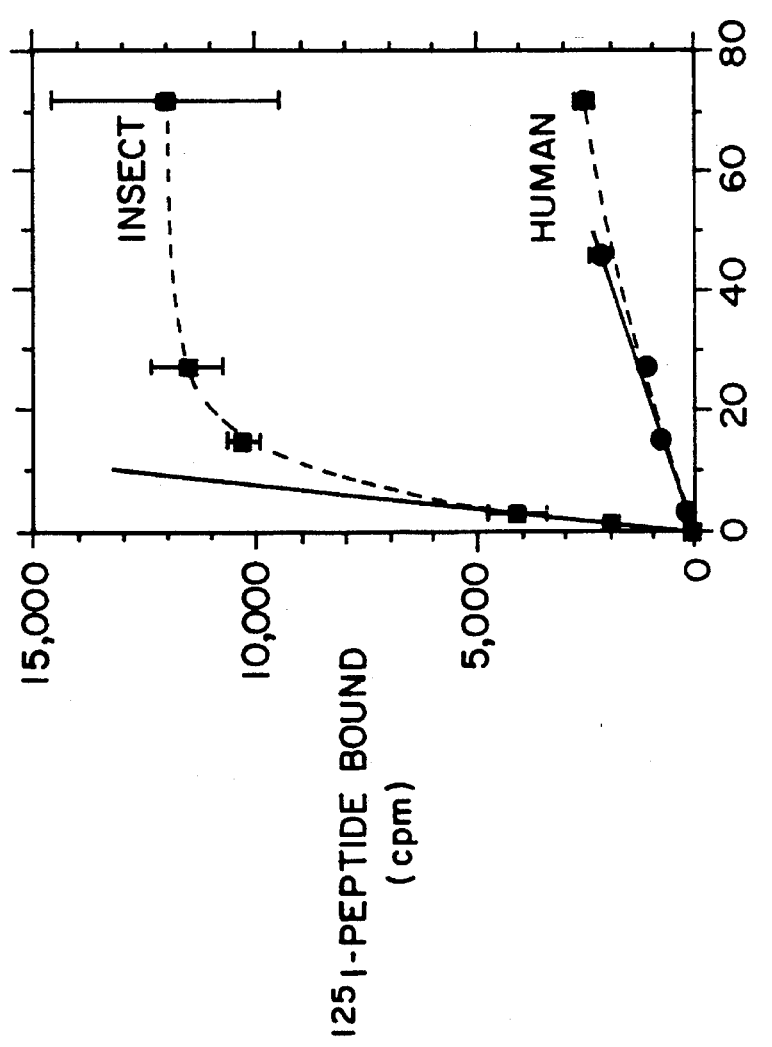
FIG. 6B
FIG. 6A

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 102 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GGGTGGAGCA   CTGGGGCTTG   GATGAGCCTC   TTCTCAAGCA   TTGGGAATTC   GATGCTCCAA          60

GCCCTCTCCC   AGAGACTACA   GAGAACTAAG   CGGCCGCGGT   AC                              102
```

( 2 ) INFORMATION FOR SEQ ID NO:2:

( i ) SEQUENCE CHARACTERISTICS:
        ( A ) LENGTH: 102 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CGCGGCCGCT TAGTTCTCTG TAGTCTCTGG GAGAGGGCTT GGAGCATCGA ATTCCCAATG    60

CTTGAGAAGA GGCTCATCCA AGCCCCAGTG CTCCACCCTG CA    102

( 2 ) INFORMATION FOR SEQ ID NO:3:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GACTTGGATC CTATAAATAT GGTGTGTCTG AAGCTCCCT    39

( 2 ) INFORMATION FOR SEQ ID NO:4:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

ACAGCTCTAG ATTACTTGCT CTGTGCAGAT TCAGA    35

( 2 ) INFORMATION FOR SEQ ID NO:5:

( i ) SEQUENCE CHARACTERISTICS:
        ( A ) LENGTH: 13 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:5:

Pro Lys Tyr Val Lys Gln Asn Thr Leu Lys Leu Ala Thr
1               5                   10

( 2 ) INFORMATION FOR SEQ ID NO:6:

( i ) SEQUENCE CHARACTERISTICS:
        ( A ) LENGTH: 11 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:6:

Pro Glu Thr Thr Glu Asn Val Val Cys Ala Leu
1               5                   10

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:7:

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:8:

```
Pro Glu Thr Thr Glu Asn
1               5
```

```
Glu Ser Ala Gln Ser Lys Met Leu Ser Gly Val
1               5                   10
```

(2) INFORMATION FOR SEQ ID NO:9:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:9:

```
Glu Ser Ala Gln Ser Lys
1               5
```

EMPTY MAJOR HISTOCOMPATIBILITY CLASS II HETERODIMERS

BACKGROUND OF THE INVENTION

The field of the invention is the major histocompatibility complex class II antigens and immune disorders.

Autoimmunity implies that an immune response has been generated against self-antigens (autoantigens). Central to the concept of autoimmunity is the breakdown in the ability of the immune system to differentiate between self- and non-self antigens. An abnormal immune response to self-antigens implies that there is a loss of tolerance.

The major histocompatibility complex (MHC) class II molecules are important for interactions between immune cells, particularly in antigen presentation to T cells. During a normal immune response, MHC molecules present a foreign antigen to a T cell as a non-self antigen. T cells respond by initiating a cascade of immune events that results in the eventual elimination of the foreign molecule. During autoimmune disease, MHC molecules present a self-antigen to the T cells as a non-self antigen, an event that also triggers T cell induced immune activation. However, in this latter case, since the immune response is directed against self-antigens it frequently results in severe damage to tissues and organs.

MHC proteins are highly polymorphic cell surface glycoproteins that bind antigenic peptides and display them at the cell surface (Rothbard and Gefter, 1991, Ann. Rev. Immunol. 9: 527). T lymphocytes initiate immune responses by recognizing a specific peptide bound to an MHC protein. Class I MHC proteins bind to endogenous peptides in the endoplasmic reticulum (Nuchtern et al., 1989, Nature 339: 223; Yewdell and Bennick, 1990, Cell 62: 203), while class II MHC proteins generally bind exogenously derived peptides in a specialized post-Golgi compartment (Guagliardi et al., 1990, Nature 343: 133; Neefjes et al., 1990, Cell 61: 171; Harding et al., 1990, Proc. Natl. Acad. Sci. USA 87: 5553; Davidson et al., 1991, Cell 67: 105; Germain and Hendrix, 1991, Nature 353: 134). Both class I and class II MHC proteins must bind peptides tightly to prevent peptide exchange at the cell surface and inappropriate immune response.

The peptide-binding sites of class I molecules are usually occupied with a mixture of peptides (Bjorkman et al. 1987, Nature 329: 506; Jardetzky et al., 1991, Nature 353: 326; Falk et al., 1991, Nature 351: 290), and class I molecules do not easily exchange or bind peptides in vitro (Chen and Parham, 1989, Nature 337: 743). Studies using mutant cell lines that do not load peptides onto class I molecules have suggested that peptide binding is required for assembly of the class I heterodimer and for stable cell surface expression (Townsend et al., 1989, Nature 340: 443; Townsend et al., 1990, Cell 62: 285; Ljunggren et al., 1990, Nature 346: 476; Ortiz-Navarrete and Hammerling, 1991, Proc. Natl. Acad. Sci. USA 88: 3594).

Class II MHC proteins isolated from lymphoid cells are very stable complexes with antigenic peptides (Buus et al., 1988, Science 242: 1045; Rudensky et al., 1991, Nature 353: 662). Less than 20% of these class II molecules will bind antigenic peptide added in vitro (Watts and McConnell, 1986, Proc. Natl. Acad. Sci. USA 83: 9660; Buus et al., 1987, Immunol. Rev. 98: 115; Jardetzky et al., 1990, Nature 353: 326; O'Sullivan et al., 1990, J. Immunol. 145: 1799; Roche and Cresswell, 1990, Ann. Rev. Immunol. 144: 1849), or in vivo (Ceppellini et al., 1989, Nature 339: 392; Busch and Rotherbard, 1990, J. Immunol. Meth. 134: 1). The peptide-binding sites on the remainder of the proteins are occupied with tightly bound peptides (Tampe and McConnell, 1991, Proc. Natl. Acad. Sci. USA 88: 4661).

SUMMARY OF THE INVENTION

The invention features compositions and methods for producing empty class II major histocompatibility heterodimers by expression in insect cell culture, and for loading these molecules with any desired antigen. The compositions and methods of the invention are superior to those previously available because they provide histocompatibility protein that can be 100% loaded with any peptide antigen, and because they provide a large amount of soluble or membrane-associated histocompatibility protein.

Accordingly, in one aspect, the invention features a pure sample of mammalian empty class II heterodimer containing an $\alpha$ and a $\beta$ polypeptide, which is either membrane-associated or in soluble form. When the heterodimer is membrane-associated, the $\alpha$ and $\beta$ polypeptides each contain the transmembrane domain that is normally present on the naturally occurring molecules. When the heterodimer is soluble, the transmembrane domain is absent from both the $\alpha$ and $\beta$ polypeptides.

By a "pure sample" is meant a heterodimer that does not have an antigen bound to it. The "antigen" to be loaded onto a heterodimer can be any substance with antigenic properties, for example, a protein or a peptide, a carbohydrate, a nucleic acid or a lipid, or any combination, fragment or combinations of fragments thereof. An "empty" heterodimer is one which does not have an antigen bound to it. A "membrane-associated" heterodimer is one which is complexed with a lipid membrane by virtue of an amino acid sequence which acts as a transmembrane domain, contained within each of the polypeptides comprising the heterodimer, and which anchors the heterodimer to a membrane. A "soluble" heterodimer is one which is not membrane-associated and wherein the polypeptides contained within the heterodimer do not contain an amino acid sequence acting as a transmembrane domain or as a cytoplasmic domain. An "antigenic peptide" is one which contains an amino acid sequence that encompasses an antigenic determinant. Such a peptide may be a full-length peptide which contains within it an antigenic determinant, or it may be a peptide whose amino acid sequence solely specifies an antigenic determinant. For the purposes of clarity, the term "antigenic peptide" will be used hereinafter to describe the molecule which can be bound to the empty heterodimer, although it is understood that this molecule need not be restricted solely to a peptide molecule.

The invention also features a baculovirus which contains DNA encoding the $\alpha$ polypeptide of the heterodimer and a baculovirus which contains DNA encoding the $\beta$ polypeptide of the heterodimer. In each case, the baculovirus contains DNA encoding either the membrane-associated or soluble form of each polypeptide.

In yet another aspect of the invention, there is described a method of producing either a membrane-associated or soluble empty major histocompatibility class II heterodimer. The method involves coinfecting insect cells with baculoviruses which contain DNA encoding the $\alpha$ and $\beta$ polypeptides. During virus replication in the cells, the genes encoding the polypeptides are expressed and the protein products are recovered from the cells or from their growth medium.

The invention also features a cell which expresses a membrane-associated or soluble major histocompatibility class II heterodimer.

Other features and advantages of the invention will be apparent from the following detailed description and from the claims.

BRIEF DESCRIPTION OF THE DRAWINGS

The drawings will first be briefly described.

FIG. 1(C and D): HLA-DR1 genes used to construct recombinant baculoviruses. Nucleotide numbering beginning at the initiation codon is indicated above the boxes. Amino acid numbering begins after the signal sequence at the N-terminus of the mature polypeptide. Portions of the amino acid sequence near the C-terminal end of the extracellular domain along with amino acid residue numbers are indicated below the boxes. DRα (FIG. 1C) and DRβ (FIG. 1D) contain the entire coding sequence of the parent cDNAs. DRαsol (FIG. 1C) and DRαsol (FIG. 1D) have been truncated just before the transmembrane domain as indicated. Open boxes indicate coding regions: SS, signal sequence; α1, α2 (FIG. 1C), β1, β2 (FIG. 1D), HLA extracellular domains; CP, connecting peptide; TM, transmembrane domain; CYTO, cytoplasmic domain.

FIG. 2(A–d) is graph of cell surface expression of DR1 in infected Sf9 cells. Baculovirus-infected Sf9 insect cells along with LG2 human lymphoblastoid cells were analyzed by flow cytometry at 48 hour post-infection. Surface expression of DR1 was detected using phycoerythrin-conjugated anti-DR1 monoclonal L243 (shaded). Background fluorescence was estimated with non-specific phycoerythrin-conjugated mouse antibody (open). (FIG. 2A) Sf9 cells infected with BV-DRα alone. (B) Sf9 cells infected with BV-DRβ alone. (FIG. 2C) Sf9 cells coinfected with BV-DRα+BV-DRβ. (FIG. 2D) LG2 cells.

FIG. 3 is a graph of the time course of expression of soluble and membrane-bound HLA-DR1 in insect cells. Sf9 cells (10$^6$ cells per ml) were coinfected with BV-DRα+BV-DRβ (squares) or with BV-DRαsol+BV-DRβsol (circles), or were singly infected with either BV-DRα or BV-DRβ alone (triangles). DR1 concentration in the extracellular medium (open symbols) or in cell lysates (closed symbols) was determined by ELISA, using the conformationally sensitive monoclonal antibody L243 as the capture antibody. Determinations with monoclonal antibody LB3.1 produced similar results. The dashed line indicates cell viability by trypan blue exclusion.

FIG. 5(A–D) is a graph of HPLC gel filtration analysis of soluble DR1 from insect and human cells. Soluble DR1 (80 μM) from insect cells was incubated in the absence (FIG. 5A) or the presence (FIG. 5B) of 500 μM HA(306–318) peptide for 86 hr at 37° C., before HPLC analysis. The elution profile of papain-solubilized DR1 from human cells (FIG. 5C) was unaltered by incubation with HA(306–318)peptide. In a separate experiment (FIG. 5D), 0.3 μM soluble DR1 from insect cells was incubated, with 1 μM [$^{125}$I]HA(306–318) peptide (open bars) or with labeled peptide and a 50-fold excess of unlabeled HA(306–318) peptide (shaded bars), and was analyzed by gel filtration HPLC. Fractions (0.5 ml) were collected, and the amount of radioactivity in each fraction was determined by gamma counting. The inset to (FIG. 1A) indicates the elution position of molecular weight standards blue dextran (void volume Vo), thyroglobulin (670,000), immunoglobulin G (158,000), ovalbumin (44,000), myoglobin (17,000), and vitamin B12 (1,300).

FIG. 6(A and B) is a graphical demonstration of the association and dissociation kinetics of antigenic peptide binding to HLA-DR1 from human and insect cells. FIG. 6A (left panel): association kinetics. Soluble DR1 isolated from insect cells (0.14 μM), or produced by papain cleavage of DR1 from human cells (0.21 μM), was incubated with 2.5 μM [$^{125}$I]HA(306–318) peptide at 37° C. At the indicated times the binding reaction was stopped and the amount of bound peptide was determined by immunoabsorption. Squares, soluble DR1 from coinfected insect cells: circles, papain-solubilized DR1 from human lymphoblastoid cells. Closed symbols, DR1+$^{125}$I-labeled HA peptide, open symbols, DR1+$^{125}$I-labeled HA peptide+20-fold excess cold HA peptide. Solid lines indicate the initial rate of peptide binding: dashed lines indicated the best fit single exponential equations, with τ=7.8 hr and a maximum of 12,000 cpm for insect-cell-produced DR1, and with τ=81 hr and an extrapolated maximum of 4,800 cpm for human-cell-produced DR1.

FIG. 6B (right panel): dissociation kinetics. DR1-peptide complexes were formed as described above, isolated by spin ultrafiltration, and diluted to 25 nM DR1 in binding buffer containing 0.25 mM unlabeled peptide. At the indicated times DR1-peptide complexes were again isolated and the amount of radiolabeled peptide remaining bound to DR1 was determined by gamma counting. Dashed lines indicated single exponential fits with τ=81 hr for DR1 from insect cells and τ=52 hr for DR1 from human cells.

DETAILED DESCRIPTION OF THE INVENTION

Expression of Heterodimers

Figures 1A, 1B:
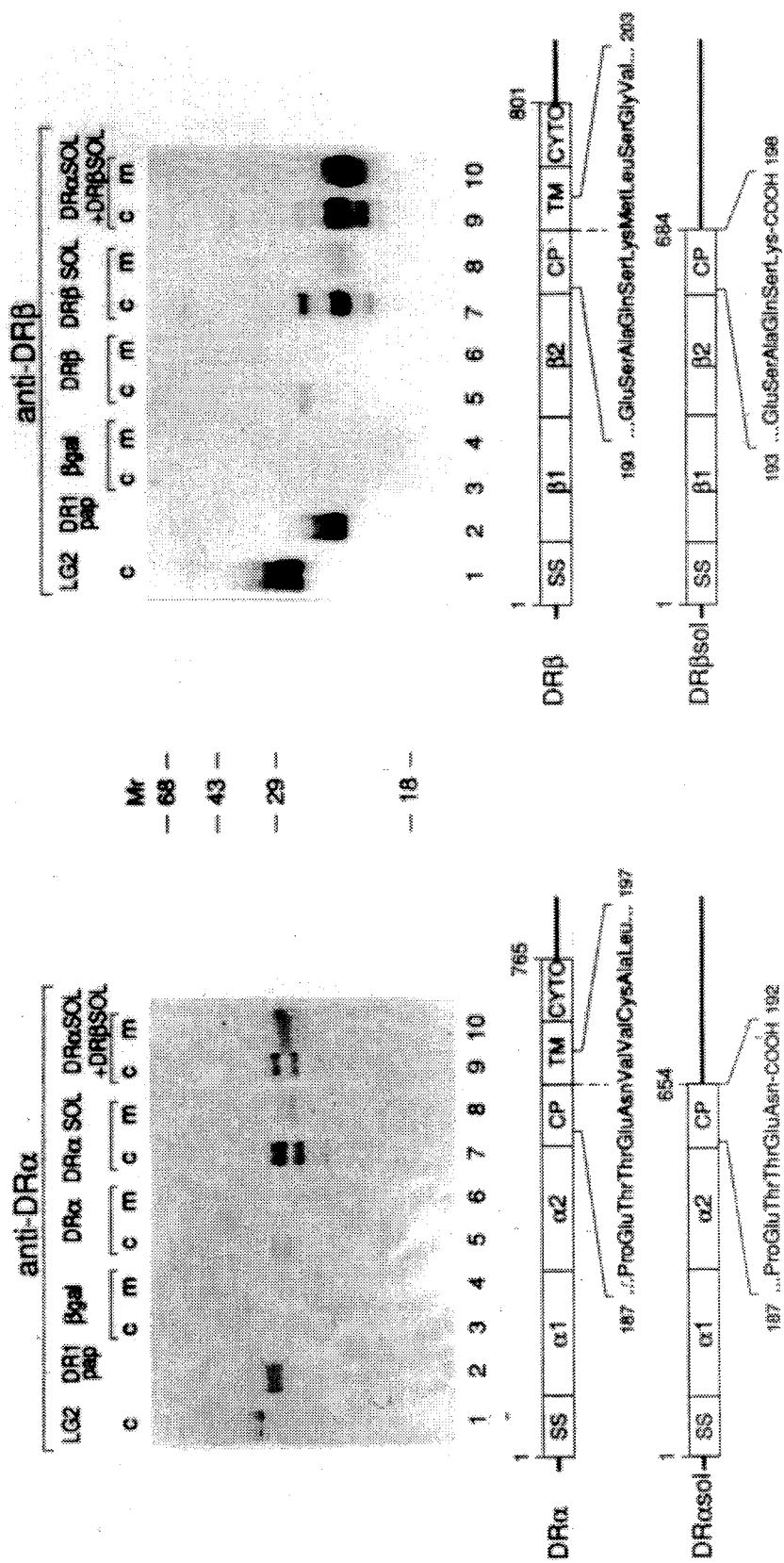
FIG. 1(A and B) depicts expression of full-length and truncated DRα and DRβ polypeptides in baculovirus-infected Sf9 insect cells. Upper panels: Western blots for DRα and DRβ. Sf9 cells were harvested 72 hour post-infection, and aliquots of cell lysate (c) and extracellular medium (m) were analyzed by 12.5% acrylamide SDS-PAGE and Western blotting with specific antisera directed against DRα (FIG. 1A) or DRβ (FIG. 1B). Lane 1, human LG2 cell lysate; lane 2, affinity-purified, papain-solubilized DR1 from LG2 cells (DR1pap); lanes 3 and 4, cell lysate and extracellular medium from Sf9 insect cells infected with control baculovirus BV-β-gal; lanes 5 and 6, cell lysate and extracellular medium from insect cells infected with either BV-DRα or BV-DRβ; lanes 7 and 8, cell lysate and extracellular medium from insect cells infected with either BV-DRβsol or BV-DRβsol; lanes 9 and 10, cell lysate and extracellular medium from insect cells coinfected with both BV-DRα and BV-DRβsol. Samples of lysates and extracellular medium represented 1×10$^5$ cells in (FIG. 1A) and 2.5×10$^4$ cells in (FIG. 1B). Papain solubilized DR1 from human cells (DR1pap) was used at 100 ng (FIG. 1A) and 25 ng (FIG. 1B) per lane.

Class II histocompatibility proteins are expressed as αβ heterodimers by insect cells (*Spodoptera frugiperda*, fall armyworm) infected with recombinant baculoviruses. The viruses carry genes coding for the α and for the β subunits of the histocompatibility protein. The protein can be produced in a membrane-associated form, or in a secreted, soluble form by alteration of the carboxy-terminus. Like the mammalian cells from which histocompatibility proteins are conventionally isolated, the insect cells glycosylate and correctly assemble the histocompatibility protein, but, unlike the mammalian cells, they do not load the binding site with tightly bound endogenous peptides. The proteins are isolated from insect cells as empty molecules by immunoaffinity and ion-exchange procedures. Antigenic peptide is loaded onto the purified molecule in vitro, and the 1:1 complex of peptide and histocompatibility protein is isolated. The compositions and methods of the invention are described in detail below.

Materials and Methods

Oligonucleotides were synthesized with a Milligen model 3700 DNA synthesizer using β-cyanoethyl phosphoroamidite chemistry, and were purified by denaturing acrylamide gel electrophoresis and reverse-phase chromatography on Sep-pack (Millipore) cartridges. Baculovirus transfer plasmids pVL1393 and pAC360-βgal and the wild-type baculovirus ACMNPV-E2 are available from In Vitrogen. Restriction enzymes and DNA modifying enzymes were obtained from New England Biolabs, Boehringer Mannheim, US Biochemicals and Promega.

Hybridoma cells secreting anti-DR monoclonal antibody L243 (1 gG$_{2a}$) were obtained from the American Type Culture Collection (ATCC #HB55) and were maintained in Dulbeccos modified Eaglets medium (DMEM: Sigma) plus 10% fetal bovine serum (FBS). As an alternative to L243, LB3.1-secreting (1 gG$_{2b}$) cells were obtained from J. Strominger (Harvard University) and were maintained in RPMI 1640 (Sigma) plus 10% FBS. For antibody, production cells were grown with immunoglobulin G-free FBS (Gibco) in roller bottle culture or in serum-free medium WHC935 medium (Amicon) in a min-Flow Path bioreactor. Antibodies were purified from clarified tissue culture medium by ammonium sulfate fractionation followed by affinity chromatography on protein A-agarose (Repligen) or protein G-Sepharose Fast Flow (Pharmacia). Phycoerythrin-conjugated L243 and control mouse immunoglobulin G were obtained from Becton-Dickinson. Rabbit antiserum against papain-solubilized DR1 was produced by Hazelton. Anti-DR1 monoclonal antibodies IVA12(β1), TAL14 1(β1), Tu36(β2), Tu39(β1), Tu43(αβ), and SG171(β1) and biotinylated monoclonal antibodies DA2 (β1), DA6. 147 (β1), DA6.321 (α), TALS. 1 (β1) were obtained from D. Vignali (Harvard University). As an alternative to these antibodies, L227(β1) and L243 (ATCC) were also used. The specificity of each antibody for DR domains is indicated in parentheses. Rabbit antisera specific for the α and β chains of DR1 was provided by D. Vignali (The Netherlands Cancer Institute). Such antisera can be prepared by any artisan skilled in the art by inoculating rabbits with publicly available α and β chains. Goat anti-rabbit or anti-mouse secondary antibodies were obtained from Boehringer Mannheim (horseradish peroxidase-labeled) and Promega (alkaline phosphate-labeled). Streptavidin-alkaline phosphatase was from Biorad.

Immunoaffinity-purified DR1 isolated from the human lymphoblastoid cell line LG2, and soluble DR1 produced by limited papain digestion of immunoaffinity-purified DR1 from LG2, were generous gifts of J. Gorga and J. Strominger (Harvard University). Glycosidases, digoxygenin-labeled lectins, and detergents were from Boehringer Mannheim. HA(306–318) peptide (NH$_2$-PKYVKQNTLKLAT-COOH) SEQ. ID NO: 5 was synthesized with an ABI model 431 peptide synthesizer using Fmoc chemistry, and was purified by reverse-phase high-pressure liquid chromatography (HPLC) on ClsProPep (Vydac) in 0.1% trifluoroacetic acid using a 40%–60% acetonitrile gradient. The purified peptide was characterized by amino acid analysis (Harvard Microsequenceing Facility) and by mass spectrometry (Harvard Spectrometry Lab) and shown to be homogenous. Peptide concentration was determined by ultraviolet absorbance using $\epsilon_{280}=1800$ M$^{-1}$cm$^{311}$.

Construction of Transfer Plasmids Carrying DRα, DRβ, Truncated DRα, and Truncated DRβ Genes cDNA clones for the α and β subunits of HLA-DR1 were DRA and DRB1*0101, GENBANK identifiers: Hummhdram.pr and Hummhldr1b.pr. Transfer plasmids carrying DRα and DRβ genes were constructed by isolation of the genes as BamHI fragments from the appropriate cDNA clones and insertion of these genes into the unique BamHI site of the baculovirus transfer plasmid pVL1393. In this vector the inserted genes are under transcription control of the strong late polyhedrin promoter. The initiation codon of the polyhedrin gene has been altered to ATT (Luckow and Summers, 1989, Virology 170: 31), so that translation is initiated at the first ATG in the inserted gene. Clones carrying DRα or DRβ inserts in the proper orientation were isolated, and the expected sequences were confirmed throughout the entire coding regions.

DRαsol (FIG. 1) was constructed by using a synthetic oligonucleotide duplex that codes for DRα sequence from the unique PstI site at nucleotide 566 to the Asn-192 codon ending at nucleotide 651, followed by the termination codon TAA, and NotI and KpnI cloning sites. The sequences of the constituent oligonucleotides were:

5'-GGGTGGAGCACTGGGGCTTGGATGAGCCTCTTCTCAAGCATTGGG<u>AATTC</u>
GATGCTCCAAGCCCTCTCCCAGAGACTACAGAGAA<u>CTAAGCGGCCGCGG</u>TAC-3'   (SEQ ID NO:1)

and

3'-ACGTCCCACCTCGTGACCCCGAACCTACTCGGAGAAGAGTTCGTAACCC<u>TTAA</u>G
CTACGAGGTTCGGGAGAGGGTCTCTGATGTCTCTTG<u>ATTCGCCGGCGC</u>-5'   (SEQ ID NO:2)

Altered sequences relative to the DRα gene are underlined; the first two substitutions are silent changes to introduce a unique EcoRI site. They synthetic duplex was inserted into pVL1393-DRα between the PstI site in the DRα gene and KpnI site downstream in the disabled polyhedrin gene. One clone carrying the insert was sequenced through the altered region and shown to have the expected sequence.

DRβsol (FIG. 1) was constructed by polymerase chain reaction-mediated amplification of the DRβ gene. The "forward" oligonucleotide primer complementary to the coding strand 5'-GACTTGGATCCTATAAATATGGTGT-GTCTGAAGCTCCCT-3' (SEQ ID. NO: 3) introduces a BamHI site upstream of the initiation ATG codon, and the reverse primer 5'-ACAGCTCTAGATTACTTGCTCTGTG-CAGATTCAGA-3' (SEQ ID NO: 4) introduces a termination TAA codon starting at nucleotide 682 followed by an XbaI cloning site. Sequences not present in the DRβ gene are underlined. The truncated gene was amplified by 10 cycles of melting (94° C., 1 min) annealing (55° C., 1 min) and extension (72° C., 3 min). The reaction product was isolated, cut with BamHI and XbaI and inserted into the corresponding restriction sites of pUC19. One of three clones sequenced had no unexpected substitutions and the DRβsol gene was excised from this clone and inserted between the BamHI and XbaI sites of pVL1393.

Construction of Recombinant Baculovirus Clones

Recombinant baculoviruses BV-βgal, BV-DRα, and BV-DRβ were produced by homologous recombination following cotransfection of $2 \times 10^6$ cells with 5 μg of plasmid and 1 μg of viral (wild-type ACMNPV-E2) DNAs, as described (Summers and Smith, 1988, A Manual of Methods for Baculovirus Vectors and Insect Cell Culture Procedures:Texas Agricultural Experiment Station Bulletin No. 1555, College Station, Tex.). Recombination efficiencies varied from 0.1% to 1%. Viral clones were isolated by limiting dilution in 96-well tissue culture plates. Recombinant viruses were identified by dot-blot DNA hybridization of alkali-lysed cells (Summers and Smith, Supra) using a $^{32}$P-labeled probe carrying both DRe and DRβ sequences. Three or four rounds of dilution and screening were required to obtain single isolates free of wild-type virus. Recombinant baculoviruses BV-DRαsol and BV-DRβsol were similarly produced and isolated except that BV-βgal viral DNA was used instead of wild-type ACMNPV-E2. This simplified the identification of nonrecombinant viruses which were easily observed by including 5-bromo-4-chloro-3-indole-β-D-galactoside (0.2 mg/ml) in the culture medium.

Sf9 Growth and Infection

Spodoptera frugiperda (Sf9) were obtained from the American Type Culture Collection (ATCC#CRL1711) and were maintained at 27° C. in TNM-FH medium (Gibco) plus 10% FBS. Viral stocks were produced by infection at low multiplicity and were stored at 4° C. Viral titers were usually greater than $10^8$ plaque-forming units per ml. For protein production, cells were grown in spinner flasks (100 ml or larger) in serum-free media SF900 (Gibco) or Excell1410 (JRH Scientific). Cells were infected at $1 \times 10^6$ cells per ml with a multiplicity of infection of 20 for each virus using the procedures described in Summers and Smith (Supra).

SDS-PAGE and Western Blotting

Cell lysates for SDS-PAGE analysis were prepared by mixing washed cells with 1/10 culture volume phosphate-buffered saline (PBS: 20 mM phosphate 130 mM NaCl [pH 7.2]) containing 1% CHAPS and a mixture of protease inhibitors (1 mM EDTA, 1 mM phenylmethylsulfonyl fluoride (PMSF), 0.1 mM iodoacetamide, 0.3 μM aprotinin, 1 μM pepstatin, 1 μM leupeptin). The mixture was stored at 4° C. for 1 hr. and nuclei and cell debris were removed by low-speed centrifugation. Samples of extracellular medium for SDS-PAGE were prepared by acetone or trichloroacetic acid precipitation. Samples for SDS-PAGE were mixed with SDS-PAGE sample buffer (Laemmli, 1970, Nature 227: 680) containing 1% SDS and 1000 mM dithiothreitol (DTT) (final concentrations) and boiled for 3 min before application to 12.5% acrylamide SDS-PAGE slab gels (7×7×0.075 cm). After electrophoresis gels were transferred to polyvinylidene fluoride (PVDF) membranes (Immobilon-P Millipore). Membranes were blocked in 3% bovine serum albumin (BSA) in PBS. DRα and DRβ polypeptides were detected using appropriate antisera followed by alkaline-phosphatase conjugated anti-rabbit serum and nitro-blue tetrazolium and bromochloroindole phosphate as described (Blake et al., 1984, Anal. Biochem. 136: 175).

Flow Cytometry

Baculovirus-infected cells were analyzed by flow cytometry at 48 hr postinfection, before significant virus-induced cell lysis. In order to avoid the strong green autofluorescence intrinsic to Sf9 insect cells, long-wavelength flurorphore R-phycoerythrin (PE) was used. At 48 hr postinfection, $10^6$ cells were pelleted, gently resuspended in 1/10 culture volume Grace's medium (Gibco), 2% FBS, 0.01% $NAN_3$, and incubated for 1 hr on ice with PE-conjugated L243 or PE-conjugated nonspecific control mouse immunoglobulin G. The cells were washed three times with Grace's medium and were finally resuspended at 1/10 the initial culture volume in PBS and fixed with 2% paraformaldehyde. Red fluorescence was measured with a Becton-Dickinson FACS-can flow cytometer.

Enzyme-Linked Immunosorbent Assay (ELISA)

The ELISA used to measure DR1 concentration was a sandwich type, with solid phase L243 or LB3.1 monoclonal antibodies used to capture native DR1, and rabbit anti-DR1 and alkaline-phosphatase-labeled goat anti-rabbit antibodies used to detect bound DR1. Ninety-six-well microtiter plates (Maxisorp, Nunc) were coated with 200 ng of purified L243 or LB3.1 monoclonal antibody in 100 mM sodium carbonate (pH 9.6) blocked with 3% BSA in PBS, and stored at 4° C. All subsequent incubations were for 30 min or 1 hr at room temperature using 0.1 ml per well and were followed by three washes with 0.05% Triton X-100 in PBS (PBST). Dilutions of samples and DR1 standards (0.1–100 ng per well) were prepared in PBST plus 0.3% BSA and applied to the plate. After binding, DR1 was detecting using rabbit anti-DR1 serum (1:50,000 in PBST plus 0.3% BSA) followed by horseradish peroxidase-coupled goat anti-rabbit antibody (15 μg/ml in PBST plus 0.3% BSA). The plate was developed with the peroxidase substrate 2.2'azino-di[3-ethyl]benzthiazoline sulfonate (ABTS, Boehringer Mannheim) in perborate-citrate-phosphate buffer. After 5–15 min, the reaction was stopped with 0.2% $NAN_3$, and the absorbance at 405 nm was measured. For quantitation of DR1, triplicate sample dilutions were compared to a standard curve produced using purified, papain-solubilized DR1 from human lymphocytes. The four-parameter binding equation (Tijssen, 1985, Practice and Theory of Enzyme Immunoassays: Laboratory Techniques in Biochemistry and Molecular Biology 15:, New York: Elsevier Science Publishers)

$$A=(A_{max}-A_{min})/(1+(C/C_{1/2})b)+A_{min}$$

where A is the absorbance caused by a sample of concentration C, and $A_{max}$, $A_{min}$, $C_{1/2}$, and b are adjustable parameters, was fit to the standard curve by a nonlinear least squares algorithm, and was used to convert sample absorbances to DR1 concentrations.

For determination of the reactivity of DR1 from insect or human cells with a panel of anti-DR1 antibodies, a direct-binding ELISA was used. Microtiter plates were coated with 200 ng per well of DR1 and blocked as above. Serial dilutions of monoclonal antibodies or biotinylated monoclonal antibodies were added to the plate; and bound antibodies were detected by alkaline-phosphatase goat anti-mouse antibodies, or with streptavidin-alkaline phosphatase, and p-nitrophenylphosphate (Harlow and Lane, 1988, Antibodies: A Laboratory Manual, Cold Spring Harbor, N.Y.). The antibody dilution that produced one-half the maximal absorbance was used to compare the affinity of each antibody for human- and insect-cell-derived DR1.

Isolation of DR1 from Coinletted Insect Cells

The procedures used to purify DR1 from insect cells were based on those developed for isolation of DR1 from human lymphoblastoid cells (Gorga et al., 1987, J. Biol. Chem. 262: 16087). Soluble DR1 was isolated from the conditioned culture medium of Sf9 insect cells coinfected with DRαsol and DRβsol. At 72 hr postinfection, cells were removed by centrifugation and the mixture of protease inhibitors was added. The culture medium was concentrated approximately 10-fold using a spiral membrane cartridge (Amicron SLY10) and used for immunoaffinity purification.

Soluble DR1 was also isolated from lysates of cells coinfected with DRαsol and DRβsol. Washed cells were lysed in 10 mM Tris-Cl (pH 8.0) containing the protease inhibitor mixture, by repeated passage through a 23 gauge needle. The lysate was centrifuged (200,000×g, 30 min, 4° C.) and the clarified lysate was enriched for DR1 by ion exchange chromatography on Q-Sepharose (Pharmacia) in 10 mM imidazole-HCl (pH 6.4) using a 50–250 mM NaCl gradient. DR1-containing fractions were pooled and used for immunoaffinity purification.

Full-length DR1 was isolated in detergent solution from BV-DRα+BV-DRβ-coinfected Sf9 insect cells. Washed cells were lysed with 1% CHAPS in PBS containing the protease inhibitor mixture. Nuclei and insoluble materials were removed by low-speed centrifugation (2,500×g, 5 min, 4° C.). The supernatant was cleared by ultracentrifugation (200,000×g, 30 min. 4° C.) and used for immunoaffinity purification.

Immunoaffinity matrices were prepared using anti-native DR1 monoclonal antibodies LB3.1 or L243. Purified antibodies were coupled at 5 mg/ml to protein A-agarose (Repligen) or to protein G-Sepharose Fast Flow using dimethyl pimelimidate as described (Harlow and Lane, 1988, Supra). Samples for immunoaffinity purification were passed through uncoupled protein A or protein G columns before application to the immunoaffinity column. Immunoaffinity columns were washed with PBS, and DR1 was eluted with 50 mM sodium cycloheylaminepropane-sulfonate (CAPS) buffer (pH 11.5). Eluted fractions were immediately neutralized with 100 mM sodium phosphate (pH 6.0). Protein-containing fractions were pooled and concentrated into PBS using a spin ultrafiltration device (Centricon-30, Amicon). For purification of the full-length protein from BV-DRα+DV-DRβ-coinfected cells, all solutions contained 1% CHAPS. The concentration of purified DR1 was determined by ultraviolet absorbance at 280 nm using an extinction coefficient of 77,000 $M^{-1}cm^{-1}$.

N-terminal sequence analysis of purified soluble DR1 from insect cells was performed after separation of the subunits by SDS-PAGE and transfer to PVDF, by automated Edman degradation, as described (Matsudaira, 1987, J. Biol. Chem. 262: 10035).

Glycosylation Analysis

For glycosidase analysis, purified DR1 samples were denatured by boiling in 1% SDS plus 1% β-mercaptoethanol, then cooled and diluted 10-fold into PBS containing protease inhibitors and 1% dodecylmaltoside. Endoglycosidase-H (EC 3.2.1.96, 0.005 U per mg of DR1), or glycopeptidase-F (EC3.2.2.18, 1U per mg of DR1), or an equivalent volume of PBS, was added, and the mixtures were incubated at 37° C. for 12 hr. The reactions were stopped by again boiling in SDS and the reaction products were analyzed by 12.5% acrylamide SDS-PAGE. For lectin analysis, purified DR1 samples were analyzed as described above for Western blotting. Parallel blots were incubated with each of the digoxigenin-labeled lectins, and then with alkaline phosphatase-labeled anti-digoxigenin, and were developed as described above. DRα and DRβ bands were identified by comparison with parallel blots analyzed with rabbit anti-DRα and anti-DRβ sera.

Peptide Binding to Purified DR1

Immunoaffinity-purified, soluble DR1 (0.05–1.0 μM) from insect or human cells was used in binding reactions, with a 2- to 10-fold molar excess HA(306–318) peptide. Standard binding conditions were 37° C. for >72 hr in PBS (pH 7.2) with 1 mM EDTA, 1 mM PMSF, 0.1 mM iodoacetamide, and 3 mM $NaN_3$. Incubation time, pH and buffer were varied in some experiments (see figure legends). SDS-PAGE analyses were performed as described above, except that larger gels (14×14×0.15 cm) were used, and some samples were not boiled prior to loading, as noted in the figure legend. After electrophoresis, proteins were detected with Coomassie brilliant blue R-250. HPLC analyses were performed using a 7.8×300 mm Waters Protein-Pak SW300 gel filtration column, equipped with a Waters 1–125 guard column, and variable wavelength absorbance detector. PBS was used as the mobile phase, with a flow rate of 0.5 ml/min.

For quantitation of peptide binding, [$^{125}$I]HA(306–318) peptide was used. Peptide (10 μg) was radiolabeled with 1 mCi of Na[$^{125}$I] and 50 μg of chloramine-T in phosphate buffer in a total volume of 50 μl for 2 min at room temperature, the reaction was stopped by the addition of excess $Na_2S_2O_5$, and the peptide was isolated by gel filtration over Sephadex G-15 (Pharmacia) in PBS. Peptide concentration in the labeled preparations was determined using a bicinchoninic acid assay by comparison with dilutions of an unlabeled peptide standard. Specific activities of the labeled peptide were 30,000–160,000 cpm/pmol in different preparations. Peptide bound to DR1 was separated from free peptide by HPLC gel filtration (as above), immunoabsorption, or spin ultrafiltration. Bound $^{125}$I-labeled peptide was measured by gamma counting.

For immunoabsorption, polystyrene microtiter wells (RIA/EIA 8-well strips, Costar) were coated overnight with 2 μg of purified L243 in 50 mM sodium carbonate (pH 9.6) and blocked with 5% nonfat dry milk. Milk was used to reduce nonspecific absorption, rather than BSA as in the ELISA assay, since radiolabeled HA(306–318) showed some binding to BSA. The DR1 binding capacity of these plates was determined to be 50 ng per well, and they were always used with subsaturating DR1 concentrations. Peptide binding mixtures (in triplicate) were added to an equal volume of blocking solution in the antibody-coated wells and were allowed to bind for 1 hr at room temperature. The wells were washed five times with PBST before gamma counting. For spin ultrafiltration, DR1 and DR1-peptide complexes were separated from free peptide by five cycles of concentration and 25-fold dilution into PBS, using Centricon-10 ultrafiltration devices (Amicon). Before use, the Centricon-10 devices were blocked with 5% nonfat dry milk and washed with PBS.

Isolation and Crystallization of Soluble DR1-Peptide Complexes

Immunoaffinity-purified soluble DR1 (0.5–1 mM) was incubated with 2- to 5-fold molar excess HA(306–318) peptide and with 1 mM EDTA, 1 mM PMSF, 0.1 mM iodoacetamide, and 3 mM $NaN_3$ at 37° C. for >72 hr. DR1-peptide complexes were separated from free peptide, aggregated DR1, and residual contaminating protein by gel filtration HPLC. The sharp peak corresponding to a molecular weight of about 50,000 was collected and concentrated by spin ultrafiltration. For crystallization, DR1 peptide complexes (5 mg/ml) were transferred to 10 mM Tris-Cl, 0.01% $NaN_3$ (pH 8.0). Crystals were obtained by vapor diffusion against 14–17% PEG 8000, 100 mM glycine (pH 3.5), using hanging drops on silanized microscope cover slips over precipitant solution in 24-well tissue culture plates.

Elution and Measurement of Bound Peptides

A procedure similar to that published for elution of peptides from class I MHC (Van Bleek and Nathanson, 1990, Nature 348: 213; Falk et al., 1991, Nature 351: 290; Jardetzky et al., 1991, Nature 353: 326) was used to elute DR1-associated peptides. DR1 samples (50 μg) were separated from low-molecular-weight material by gel filtration HPLC as above, except that 170 mM aqueous ammonium acetate was used as the mobile phase. DR1-containing fractions from each sample were pooled, and any residual low-molecular-weight material was removed by three cycles of 25-fold concentration and dilution into 170 mM aqueous ammonium acetate using a Centricon-30 ultrafiltration device as above. Bound peptides were eluted from the final concentrate by 25-fold dilution into 10% acetic acid and incubation at 70° C. for 15 min. The samples were cooled and concentrated once again. The final filtrate provided the pool of peptides eluted by acid denaturation. Filtrates were concentrated to 100 μl by vacuum centrifugation, and a portion was used for amino acid analysis on an ABI 420A/130A derivatizer/HPLC after hydrolysis with 6N HCl for 24 hr in vacuo. A sample of 170 mM ammonium acetate was processed in parallel through the HPLC, washing, elution, and analysis steps, to control for background and nonpeptidic reactivity.

Results

Recombinant Baculoviruses Direct the Synthesis and Secretion of DRαβ Heterodimers in Coinfected Sf9 Cells Recombinant baculoviruses carrying full-length genes for the α and β subunits of human DR1 and (BV-DRα and DV-DRβ), or carrying truncated genes (BV-DRαsol and BV-DRβsol), were generated by homologous recombination in the insect ovarian cell line Sf9 (fall armyworm, *Spodoptera frugiperda*). The truncated genes code for proteins of 192(α) and 198(β) residues, which terminate just before the beginning of the predicted transmembrane spans (FIG. 1, bottom panels). Insect cells infected with BV-DRα or with BV-DRβ expressed polypeptides of the expected apparent molecular weight, which reacted with antisera specific for the appropriate subunit of DR1 (FIG. 1, lanes 5). No reactivity was observed in the extracellular medium (FIG. 1, lanes 6), nor in insect cells infected with a control baculovirus, BV-μgal (FIG. 1, lanes 3 and 4).

Insect cells infected with BV-DRαsol or BV-DRβsol, which carry the truncated genes, expressed polypeptides that exhibited somewhat faster mobility on SDS-PAGE (FIG. 1, lanes 7) than the full-length forms, as expected for the removal of the transmembrane and cytoplasmic domains. The truncated constructs were expressed at a significantly greater level than the full-length proteins. A fraction of the protein produced in the singly-infected cells was secreted into the extracellular medium (FIG. 1, lanes 8). The protein retained within the cells exhibited multiple bands per subunit by SDS-PAGE, probably due to incomplete signal sequence cleavage and partial glycosylation, but the secreted protein exhibited predominantly one band per subunit. In cells coinfected with both BV-DRαsol and DV-DRβsol, secretion into the extracellular medium was much more efficient (FIG. 1, lanes 9 and 10).

The differences in mobility on SDS-PAGE between the subunits of DR1 expressed in insect cells and those of full-length DR1 (FIG. 1, lanes 1) or papain-solubilized DR1 (FIG. 1, lanes 2) produced by human cells are due to differential glycosylation in the insect cell and human cell lines. Both the α and β chains of the full-length and truncated forms of DR1 from insect cells were sensitive to endoglycosidase-H and glycopeptidase-F (Table 1). Both α and β chains bound GNA lectin but not SNA, MAA, DSA, or PNA lectins, indicating that both chains contain high-mannose, N-linked polysaccharides. In contrast, DR1 isolated from human cells carries a complex, sialated polysaccharide on each chain, along with a second, nonsialated polysaccharide on the α chain (Table 1 and Shackelford and Strominger, 1983, J. Immunol. 130: 274). After deglycosylation, the subunits of full-length and truncated DR1 from insect cells exhibited the same mobility as the corresponding deglycosylated subunits of intact or papain-solubilized DR1 from human cells.

Sf9 insect cells coinfected with the full-length constructs, BV-DRα+BV-DRβ, express DR1 on the cell surface as detected by flow cytometry using monoclonal antibody L243 (FIG. 2C). This antibody recognizes a conformational determinant on the correctly folded DR1 heterodimer (Lampson and Levy, 1980, J. Immunol. 125: 293; Gorga et al., 1987, J. Biol. Chem. 262: 16087). No reactivity was observed with Sf9 cells singly infected with BV-DRα alone (FIG. 2A) or with BV-DRβ alone (FIG. 2B). The surface expression of DR1 on the coinfected SF9 insect cell surface was weaker and more heterogeneous than that exhibited by LG2, a human lymphoblastoid cell line (FIG. 2D).

The time course of DR1 expression in insect cells was monitored by enzyme-linked immunosorbent assay (ELISA) using the anti-native DR1 monoclonal antibody L243 (FIG. 3). DR1 expression in BV-DRα+BV-DRβ-coinfected cells increased from 24 to 48 hr postinfection, then remained relatively constant (closed squares). DR1 could not be detected in the extracellular medium (open squares). No L243 reactivity was observed in lysates of singly-infected cells (shaded triangles), indicating that this antibody does not recognize DRα or DRβ monomers, or any $α_2$ or $β_2$ homodimers that may be produced by the singly infected cells. Similar results were obtained with LB3.1 (Gorga et al., 1986, Cell. Immunol. 103: 160), another conformation-sensitive monoclonal antibody that recognizes the DRαβ heterodimer. Insect cells coinfected with the truncated constructs, BV-DRαsol and BV-DRβsol, produced heterodimeric DRαβ complex that was detected in cell lysates (closed circles) and also in the extracellular medium (open circles). Secretion of DR1 to the extracellular medium significantly lagged behind expression within the cell and continued to increase very late in infection. The overall expression level of soluble DR1 (cells plus medium) remained fairly constant after 48 hr postinfection, at approximately 2 mg per liter of culture medium, more than six times the expression level of the full-length, membrane-bound form.

Purification of DR1 from Insect Cells

Figure 4:
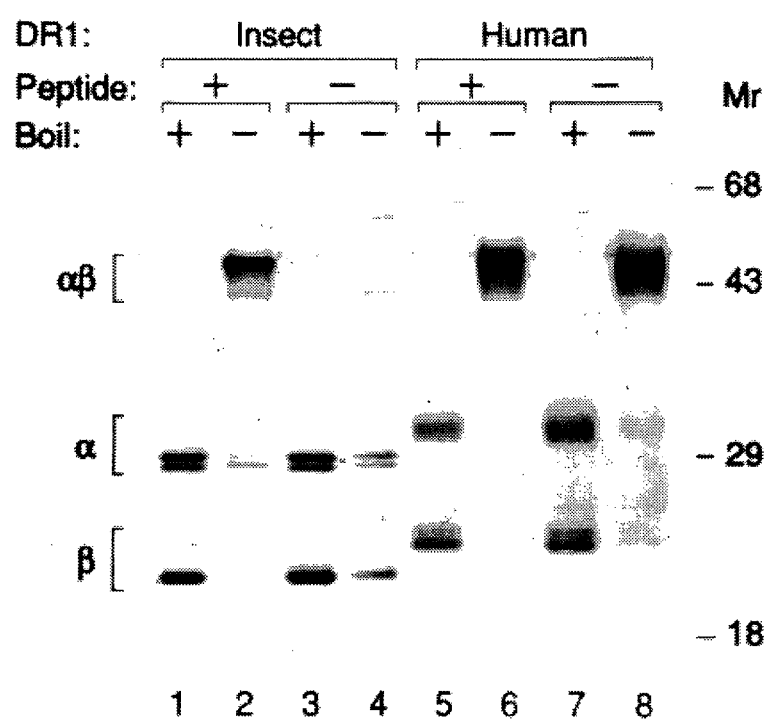
FIG. 4 is a gel depicting the analysis of soluble DR1 from insect and human cells. Soluble DR1 (80 μM) from insect cells (lanes 1–4) or papain-solubilized DR1 from human cells (lanes 5–8) was incubated in the presence (lanes 1, 2, 5 and 6) or absence (3, 4, 7, and 8) of 360 μM HA(306–318) peptide, for 100 hr at 37° C. After incubation, samples were mixed with SDS-PAGE loading buffer (final [SDS]=1%). One half of each sample was boiled for 3 min before loading (odd lanes); the other half was loaded without boiling (even lanes). Samples were analyzed by SDS-PAGE on 12.5% polyacrylamide with Coomassie brilliant blue R250 detection. Positions of molecular weight markers BSA (68000), ovalbumin (43000), carbonic anhydrase (29000), and β-lactoglobulin (18400) are indicated at right.

Insect cell cultures were harvested for protein purification at 72 hr postinfection. Soluble DR1 (1–2 μg per ml of culture) was isolated from the extracellular medium of coinfected cells in 80%–90% yield by immunoaffinity chromatography using monoclonal antibodies that recognize the native DR1 heterodimer (LB3.1 or L243). No DRα or DRβ subunits could be detected on Western blots of the material that did not bind to the affinity column, indicating that all of the secreted DRα and DRβ was present as αβ heterodimer. The immunoaffinity-purified soluble DR1 exhibited predominantly two bands (DRα and DRβ) by SDS-PAGE, along with a significant but variable amount of a second DRα band (FIG. 4, lane 1). The three bands were subjected to N-terminal sequencing. Both DRα bands had the sequence $NH_2$-IKEEH . . . , and the DRβ band had the sequence $NH_2$-GDTRP . . . These are the N-termini expected for the mature subunits, indicating that the native DR1 signal sequences were efficiently removed by the insect cell. The purified DR1 was tested against 13 monoclonal antibodies that recognize native DR1 from human cells. Each of the antibodies tested, DA2(β1-specific), DA6.147(α), DA6.231(β1), IVA12(β1), L227(β1), SG171(β1), TAL8.1(β1), TAL14.1(β1), Tu36(β2), Tu39(β1), and Tu43(αβ), as well as the antibodies used for affinity purification L243(α) and LB3.1(α), bound to the soluble, insect-cell-derived DR1.

Approximately half of the total soluble DR1 produced by BV-DRαsol+BV-DRβsol-coinfected cells was retained within the cells. This material could be isolated from a lysate of coinfected cells by ion exchange and immunoaffinity chromatographies. Soluble DR1 isolated from cell lysates behaved similarly to soluble DR1 isolated from the extracellular medium. Full-length DR1 (0.1 µg/ml of culture) could be isolated in detergent solution from lysates of BV-DRα+BV-DRβ-coinfected cells, by including 1% 3-[(3-choamidopropyl)dimethylammonio]-1-propanesulfonate (CHAPS) in all solutions throughout the purification procedure.

Purified Soluble DR1 is Stabilized by Antigenic Peptide

DR1 isolated from human lymphoblastoid cells is substantially resistant to dissociation by SDS at room temperature, and the α and β chains migrate as a heterodimer on SDS-PAGE if the samples are not boiled prior to loading (FIG. 4, lane 8; Gorga et al., 1987, J. Biol. Chem. 262: 16087). After boiling in SDS, the α and β subunits disassociate (FIG. 4, lane 7). In contrast, the soluble DR1 secreted from coinfected insect cells was sensitive to dissociation by SDS at room temperature, and migrated mostly as monomeric α and β chains, along with several faint bands near the position expected for the heterodimer (FIG. 4, lane 4). After boiling, soluble DR1 from insect cells migrated as the expected α and β monomers (FIG. 4, lane 3). Preincubation with an antigenic peptide from influenza hemagglutinin, HA(306–318), caused the soluble DR1 from insect cells to become resistant to SDS-induced dissociation. Soluble DR1 from insect cells, incubated with HA(306–318) peptide and subsequently treated with SDS at room temperature (FIG. 4, lane 2), migrates as a strong band that corresponds to the αβ heterodimer seen with DR1 from human cells. After boiling, the subunits dissociate (FIG. 4, lane 1). Incubation of DR1 from human lymphoblastoid cells with peptide had no effect on the stability to SDS-induced dissociation (FIG. 4, lanes 5 and 6).

While the DR1 isolated by immunoaffinity purification appeared to be substantially free of contaminating proteins by SDS-PAGE, it eluted from a gel permeation column in a number of peaks with apparent molecular weights of 50,000 and greater (FIG. 5A). Each of these peaks contained material that reacted with anti-DRαβ antibodies. After incubation for 72 hr at 37° C. with antigenic peptide HA(306–318), most of the protein eluted in a single peak corresponding to 50,000 daltons (FIG. 5B), as expected for the DRαβ heterodimer and as seen with DR1 isolated from human lymphoblastoid cells (FIG. 5C). Incubation of DR1 from insect cells without the addition of peptide had no effect on its aggregation behavior. The aggregation was not a result of the isolation procedure, as whole conditioned medium also exhibited multiple, DR1-containing peaks. [$^{125}$I]HA(306–318) peptide included with soluble DR1 from insect cells in the incubation mixture comigrated with the strong DR1 αβ peak (FIG. 5D, open bars). Radiolabeled peptide binding could be competed with an excess of unlabeled peptide (solid bars). The effect of added peptide in converting the heterogenous DR1 isolated from insect cells (FIG. 5A) to a mostly homogeneous species (FIG. 5B) thus occurs through peptide binding to the DR1 molecule.

Gel filtration HPLC was used to isolate the complex of soluble, insect-cell-derived DR1 with HA(306–318) peptide. The purified DR1-peptide complex retained binding to all of the anti-DR1 monoclonal antibodies described above. DR1-HA(306–318) peptide complexes were crystallized by vapor diffusion from polyethylene glycol, under conditions previously developed for crystallization of DR1 from human cells (Gorga et al., 1991, Res. Immunol. 142: 401) These crystals were morphologically similar to those produced from papain-solubilized DR1 isolated from human lymphoblastoid cells.

The SDS-PAGE (FIG. 4) and HPLC gel filtration (FIG. 5) results indicate that DR1 isolated from insect cells was less stable to denaturation and aggregation that DR1 isolated from human lymphoblastoid cells. In both assays, preincubation of the insect-cell-derived DR1 with antigenic peptide caused it to behave similarly to DR1 from human cells. In contrast, incubation of human-cell-derived DR1 with peptide had no effect on its behavior in HPLC gel filtration or SDS-PAGE, presumably because the protein as isolated is already saturated with tightly bound peptides.

Binding of Antigenic Peptide to Soluble DR1 from Insect Cells

The kinetics of radioiodinated HA(306–318) peptide binding to DR1 were measured at pH 7.2 and 37° C. for soluble DR1 produced by coinfected insect cells (FIG. 6, left panel, squares) and by human lymphoblastoid cells (circles). The initial rate of peptide binding to insect-cell-derived DR1 was 0.11 mol peptide per mole DR1 per hour, significantly faster than the 0.0093 mol peptide per mole DR1 per hour observed for human-cell-derived DR1. These initial rates correspond to pseudo-first-order rate constants of 12 $M^{-1}s^{-1}$ for DR1 from insect cells and 1.0 $M^{-1}s^{-1}$ for DR1 from human cells. The extent of radiolabeled HA(306–318) peptide binding to DR1 from insect and human cells was determined from the data in FIG. 6 (left panel). At times after 24 hr, the amount of peptide bound to the insect-cell-produced DR1 was 1.0±0.3 mol peptide per mole DR1. For human-cell-produced DR1 the (extrapolated) maximum extent of binding was 0.2±0.1 mole peptide per mole DR1.

For measurement of dissociation kinetics (FIG. 6, right panel), DR1 samples were equilibrated with excess [$^{125}$I] HA(306–318) peptide for 73 hr at 37° C. After this time, DR1-peptide complexes were separated from free peptide, diluted into buffer containing excess unlabeled peptide, and returned to 37° C. Samples were removed at the indicated times, and the amount of peptide remaining bound to DR1 was measured. The kinetics of peptide dissociation were extremely slow for DR1 from either source, and no significant difference in dissociation rate were observed over 300 hr. The dissociation data for DR1 from both sources are consistent with a first-order dissociation constant of about $4 \times 10^{-6}$ s$^{-1}$.

The pH dependence of peptide binding of DR1 from human and insect cells was also determined. Binding of excess [$^{125}$I]HA(306–318) peptide to DR1 was measured after 72 hour incubation of 37° C., for soluble DR1 from human cells (FIG. 7, solid bars) and from insect cells (shaded bars). Open and hatched bars show binding in the presence of excess unlabeled peptide. Peptide binding to human lymphoblastoid-cell-derived DR1 increased at lower pH. In contrast, peptide binding to insect-cell-derived DR1 was relatively independent of pH. At every pH tested, insect cell DR1 bound more peptide than DR1 from human lymphoblastoid cells. The extent of peptide binding observed for the insect-cell-derived DR1 corresponds to 1.1±0.2 mol peptide per mole protein. For the DR1 isolated from human cells, the extent varied from 0.06 (pH 8) to 0.3 (pH 4).

The measurements of peptide binding capacity were repeated using different preparations of [$^{125}$I]HA(306–318) peptide and DR1 from insect and human cells (Table 2). Soluble DR1 produced in insect cells reproducibly bound nearly a stoichiometric amount of peptide (0.90±0.15 mol peptide per mole DR1), while DR1 from human cells bound 5-fold less peptide (0.17±0.07 mol peptide per mole DR1). The low binding capacity, slow association kinetics and pH dependence of peptide binding for class II molecules isolated from mammalian cells are all believed to be due to the presence of tightly bound peptides occupying the antigen-binding site, which must dissociate before exogenously added peptide will bind (Buus et al., 1986, Cell 47: 1071; Roche and Cresswell, 1990, J. Immunol. 144: 1799; Tampe and McConnell, 1991, Proc. Natl. Acad. Sci. USA 88: 4661). Taken together, the increased peptide binding capacity, increased binding rate, and decreased pH dependence of peptide binding for DR1 produced in insect cells indicate that, as isolated, the antigen-binding site is largely empty.

To confirm this result, we directly measured the amount of endogenous peptide bound to DR1, using a procedure previously used to characterize peptides bound to class I and class II molecules (Van Bleek and Nathanson, 1990, Nature 348: 213; Falk et al., 1991, Nature 351: 290; Rudensky et al., 1991, Nature 353: 662). A pool of bound peptides was released from the DR1-binding site by acid denaturation, isolated by spin ultrafiltration, and finally quantitated by amino acid analysis. Papain-solubilized DR1 isolated from human cells carried the equivalent of 14 amino acid residues per mole (Table 2). Full-length DR1 from human cells gave essentially the same result. This corresponds to approximately 95% occupancy, with endogenous peptides having an average length of 15 residues. As a control, soluble DR1 from insect cells was analyzed after loading with HA(306–318) peptide. The isolated DR1-peptide complexes carried 13 amino acid residues per mole DR1, consistent with the length of the HA(306–318) peptide and a 1:1 molar ratio of bound peptide to DR1. In contrast, no amino acid residues were detected in the pool from soluble DR1 from insect cells above the reactivity observed in a buffer blank.

Using the methods described above, an ordinary artisan skilled in the art can generate empty MHC class II heterodimers from any mammalian species that encodes such proteins, for example, a mouse a rat, or a rabbit etc. Heterodimers comprising an α and a β chain are known in these species. The artisan, following the directions described above for the expression of the human heterodimer, can clone the genes encoding α and β peptides from other species of mammals into a suitable plasmid and generate baculoviruses that encode one or other of the peptides. Insect cells when coinfected with these baculoviruses should express either membrane-associated or soluble heterodimers which are empty, and which can be loaded with a suitable antigenic peptide according to the methods of the invention.

TABLE 1

Glycosylation of DR1 Produced in Human and Insect Cells

| | | DR1 Reactivity | | | |
|---|---|---|---|---|---|
| | | Insect | | Human | |
| Assay | Specificity | α | β | α | β |
| Glycosidase sensitivity | | | | | |
| Endoglycosidase H | High Mannose or hybrid | + | + | +/− | − |
| Glycopeptidase F | Most N-linked | + | + | + | + |
| Lectin reactivity | | | | | |
| GNA (*Galanthus nivalis* agglutinin) | ManαMan | + | + | − | − |
| SNA (*Sambucus nigra* agglutinin) | SAα(2–6)Gal | − | − | + | + |
| MAA (*Maackia amurensis* agglutinin) | SAα(2–3)Gal | − | − | − | − |
| DSA (*Datura straminium* agglutinin) | Galβ(1–4)-GlcNAc | − | − | + | − |
| PNA (peanut agglutinin) | Galβ(1–3)-GalNAc | − | − | − | − |

For glycosidase analysis, purified DR1 samples were denatured, digested with the appropriate glycosidase, and analyzed by SDS-PAGE. A difference in mobility in the glycosidase-treated samples relative to mock-digested samples was scored as positive. For lectin analysis, purified DR1 samples were analyzed by SDS-PAGE and Western blotting using labeled lectins. In both assays, full-length and soluble DR1 behaved identically. The expected oligosaccharide specificity is shown beside the name of each glycosidase or lectin (Man, mannose: SA, sialic acid: Gal, galactose: GlcNAc, N-acetylglucosamine: GalNAc, N-acetylgalactosamine).

TABLE 2

Stoichiometry of Peptide Binding to HLA-DR1 from Human and insect Cells

| DR1 Source | [$^{125}$I]HA(306-318) Peptide Bound (mol peptide/mol DR1) | Peptide Released by Acid Treatment (mol amino acid residue/mol DR1) |
|---|---|---|
| Human | 0.17 ± 0.07 | 14 |
| Insect | 0.90 ± 0.1 | ND |
| Insect (pre-loaded) | — | 13 |

Figure 7:
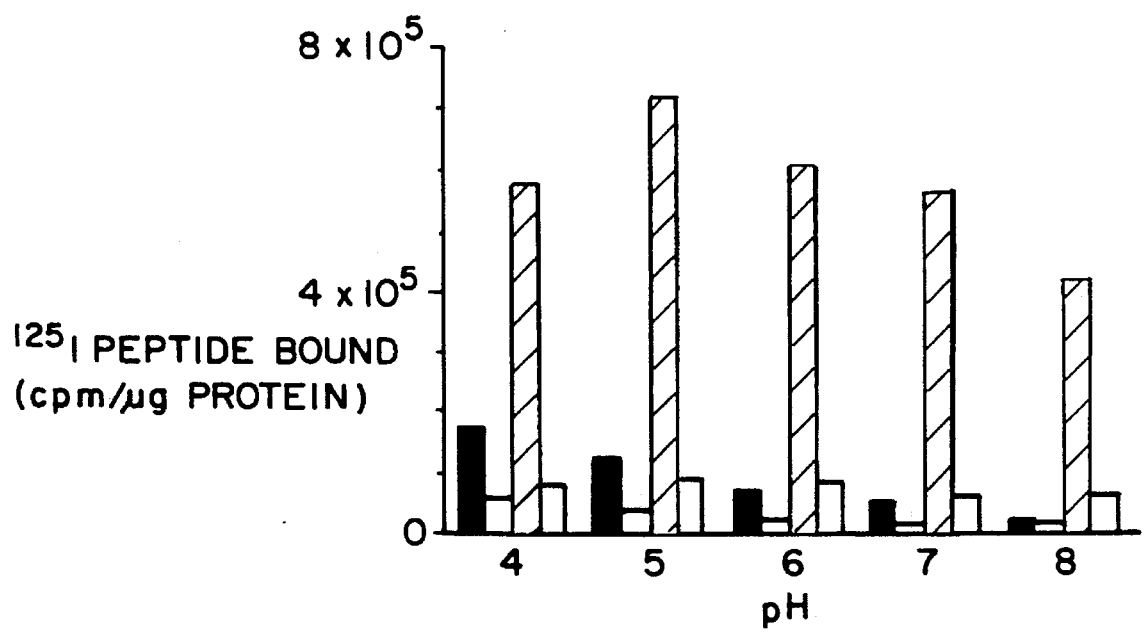
FIG. 7 is a histogram depicting pH dependence of antigenic peptide binding to HLA-DR1 from human and insect cells. Soluble DR1 produced by insect cells (0.2 μM, shaded bars) or prepared by papain digestion of DR1 purified from human cells (0.35 μM, solid bars) was incubated with 1.8 μM [$^{125}$I]HA(306–318) peptide at 37° C., in 0.1M sodium citrate-phosphate buffer at the indicated pH. After 96 hr, the amount of radioactive peptide bound to DR1 was determined by spin ultrafiltration. Radiolabeled peptide binding in the presence of 25 μM unlabeled peptide is indicated by open bars for DR1 from human cells and by lightly hatched bars for DR1 from insect cells.

The extent of [$^{125}$I]HA(306-318) peptide binding to soluble DR1 produced in insect cells and in human cells was determined for the experiments shown in FIGS. 5, 6, and 7 (pH 7 values only) and in four other trials. In each experiment, DR1 samples from insect and human cells were treated in parallel. Occupancy values for $^{125}$I-labeled HA peptide are given as the ratio of moles peptide bound per mole DR1, determined using the measured specific activity of the [$^{125}$I]HA(306-318) preparation and the concentration of DR1 determined by ELISA or absorbance at 280 nm. Values are the average of seven trials with the observed standard deviation. The amount of endogenous peptide bound to soluble DR1 was determined for papain-solubilized human DR1 and secreted insect cell DR1, and also for insect cell DR1 preloaded with HA(306-318) peptide. Bound peptides were released by acid treatment and isolated by spin ultra-centrifugation. Occupancy values are given as the ratio of moles amino acid residue in the peptide fraction, determined by amino acid analysis, per mole DR1, determined by absorbance at 280 nm. ND, none detected above the background reactivity observed for a buffer blank. Detection limit was approximately 5 amino acid residues per mole DR1.

Advantages of the Invention

The biological and immunological properties of histocompatibility proteins are largely defined by the antigenic peptide that is bound to them. All previous methods for producing class II histocompatibility proteins have provided material that contains a mixture of antigenic peptides (Buus et al., 1988, Science, 242: 1045; Rudensky et al., 1991, Nature, 353, 662), which can be only partially loaded with a defined antigenic peptide (Watts and McConnell, 1986, Proc. Natl. Acad. Sci. USA 83: 9660; Buus et al., 1987, Immunol. Rev. 98: 115; Ceppellini et al., 1989, Nature 339: 392; Busch et al., 1990, J. Immunol. Meth. 134: 1; Jardetzky et al., 1990, EMBO J. 9: 1797; O'Sullivan et al., 1990, J. Immunol. 145: 1799; Roche and Cresswell, 1990, J. Immunol. 144: 1849). Previous efforts to produce soluble MHC class II heterodimers by recombinant methods have been unsuccessful (Traunecker et al., 1989, Immunol. Today, 10: 29). The methods described in the invention provide empty class II histocompatibility proteins, which can be completely loaded with any desired antigenic peptide. In addition, the methods provide soluble histocompatibility proteins without the use of proteases and provide better yields of histocompatibility protein than current methods. Furthermore, the process is more economical and allows the protein sequence to be manipulated in any desired manner.

Uses of the Invention

The compositions and methods of the invention are useful for the treatment of humans with any disease in which an immune response to a protein causes unwanted symptoms. Thus the compositions and methods of the invention may be used to treat autoimmune disease. During autoimmune disease, T cells activated by MHC class II self-antigenic peptide complexes initiate an immune response directed against the body's own antigenic peptides in tissues and organs. However, binding of T cells to large quantities of MHC-antigenic peptide complexes has been shown to have the opposite effect in that the T cells become inactivated (Quill and Schwartz, 1987, J. Immunol. 138: 3704). While the mechanism by which this inactivation is induced is not understood, two separate theories might explain this phenomenon. High concentrations of MHC-antigenic peptide complexes when bound to T cells may simply saturate T cell receptors for that complex, thus competitively blocking the T cells' ability to bind to an identical MHC-antigenic peptide complex present in tissues and organs. Similarly, although somewhat distinct, saturation of T cell receptors with MHC-antigenic peptide complexes may induce a state of clonal anergy, wherein the clone of T cells to which the peptides are bound become incapable of activating subsequent immune events required for an immune response (Quill and Schwartz, 1987, J. Immunol. 138: 3704).

Using the methods and compositions described above it is now possible to prepare large quantities of membrane-associated or soluble MHC heterodimers that have bound to them an antigenic peptide of choice. Such an antigenic peptide might be one which triggers an autoimmune reaction in a patient with an autoimmune disease. Treatment of the patient with such MHC-antigenic peptide complexes may induce clonal anergy, or otherwise diminish or eliminate the T cell's ability to promote the autoimmune reaction.

The compositions and methods of the invention may also be used to specifically destroy autoreactive T cells. Heterodimer-antigenic peptide complexes, that are themselves conjugated to a toxin molecule, may be used to target the toxin to the autoreactive T cells, whereupon the toxin would then induce death of the T cells.

The heterodimer-antigenic peptide complex of the invention may also be used to vaccinate a patient with an antigenic peptide that when administered to the patient in the absence of the heterodimer, is incorrectly processed by the antigen-presenting cells in the body. The heterodimerantigenic peptide complex may be administered to the patient, either in solution or attached to a solid support, as an artificial antigen-presenting cell, capable of inducing a protective immune response in the patient.

The compositions and methods of the invention may also be used as a research or a diagnostic tool to identify the presence of, and to isolate T cells that are reactive with a particular heterodimer-antigen complex. In order to determine the origin and function of clonal lines of T cells and to examine their role in autoimmune disease, it is often necessary to isolate these cells in a pure form, i.e., separated from all other cells in the population, including other T cells of a different clonal origin. The compositions and methods of the invention can easily be used to isolate T cells that are reactive to a specific self-antigen, without having to go through the more conventional yet cumbersome process of first obtaining a monoclonal antibody directed against the particular T cell receptor epitope expressed by those T cells. Briefly, a population of lymphocytes are obtained from a mammal by conventional means. The self-antigen in question is complexed to empty heterodimers using the methods described above. The heterodimer has a dye, e.g., a fluorescent dye, conjugated to it using methods standard to those in the art. For example, conjugation can be accomplished using standard methods for conjugation of dyes to antibodies such as those described in Stites and Terr (1991, Basic and Clinical Immunology, Appleton and Lange) or in Harlow and Lund (Supra). The lymphocytes are incubated in the presence of heterodimer-antigen complex and only T cells that are reactive to the self-antigen present in the heterodimer complex will bind to the complex, thus becoming labeled with the dye. Labeled cells are then separated from unlabeled cells by conventional cell-sorting flow cytometry. Thus the compositions and methods of the invention provide a rapid and easy method for the purification of T cell clones that are reactive to self-antigens.

In a manner similar to that described above, the compositions and methods of the invention can be used as a diagnostic tool determine the onset of autoimmune disease in a patient, and/or to follow the progress of the disease in that patient. For example, lymphocytes obtained from a patient can be reacted with dye-labeled heterodimer-self-antigen complex without further purification. Cells that have either bound the complex or not bound the complex can be separated from free unbound complex by several cycles of centrifugation and washing. The cells can then be examined by fluorescence microscopy for the presence of the dye. If the cells are counterstained with a dye of a different color which stains all cells, for example rhodamine or Texas red, then it is possible to quantitate the number of T cells which have bound the heterodimer. Similarly, quantitation can be accomplished using flow cytometry as described above. Thus the presence of and the number of self-antigen reactive T cells can be determined in a sample obtained from a patient suspected of having an autoimmune disease. In order to monitor progression of the disease in a patient, or to monitor T cell activity in patients receiving treatment for the disease, samples can be obtained periodically and analyzed as described above. Such sampling, which in the majority of cases will involve obtaining circulating lymphocytes from the patient's blood, is a relatively painless and non-invasive procedure.

Use of the compositions and methods of the invention is not limited to the study of autoimmune disease in humans.

Where animal models of autoimmune disease are available, or become available, the compositions and methods of the invention provide an invaluable research tool to further examine the disease process, thus generating information that can then be used to eliminate or diminish the severity of such a disease in humans.

Diseases that are potentially treatable using the compositions and methods of the invention, all of which have been linked to the major histocompatibility class II molecules, are presented below. The autoreactive antigenic peptide, where it is known or suspected, is given in parentheses. The actual antigenic peptide used for forming the complex with class II might be derived from these peptides.

Multiple sclerosis (myelin basic protein)
Myasthenia gravis (acetylcholine receptor)
Systemic lupus erythematosus (DNA)
Glomerulonephritis or Goodpasture's syndrome (type IV collagen)
Insulin-dependent diabetes mellitus (insulin receptor)
Autoimmune hemolytic anemia (erythrocyte membrane proteins)
Autoimmune thrombocytopenic purpura (platelet membrane proteins)
Grave's disease (thyroid stimulating hormone receptor)
Pernicious anemia
Rheumatoid arthritis
Dermatitis herpetiformis
Celiac disease
Sicca syndrome
Idiopathic Addison's disease
Idiopathic membranous nephropathy
Narcolepsy
Optic neuritis
Postpartum thyroiditis
Hashimoto's thyroiditis
Juvenile rheumatoid arthritis.

MHC heterodimer-antigenic peptide complexes can be administered parenterally, for example intravenous, subcutaneous, intramuscular, intraorbital or intraocular administration. The complexes can be formulated for parenteral administration to humans or other mammals in therapeutically effective amounts (e.g., amounts which eliminate or reduce the patient's pathological condition) to provide therapy for the diseases described above.

The complexes provided herein can be formulated into pharmaceutical compositions by admixture with pharmaceutically acceptable non-toxic excipients and carriers. Such compositions may be prepared for use in parenteral administration, particularly in the form of liquid solutions or suspensions.

The complexes may conveniently be administered in unit dosage form and may be prepared by any of the methods well known in the pharmaceutical art, for example as described in *Remington's Pharmaceutical Sciences*. Formulations for administration may contain as common excipients sterile water or saline, cyclodextrans, polyalkylene glycols, such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the peptides. Other potentially useful delivery systems for these complexes include ethylene-vinyl acetate copolymer particles, osmotic pumps, implantable infusion systems, and liposomes. Formulations for administration may include a stabilizing agent, such as human serum albumin, as well as a permeation enhancer, such as glycocholate.

The concentrations of the complexes described herein in a therapeutic composition will vary depending upon a number of factors, including the dosage of the complex to be administered and can be determined on a case by case basis.

---

I claim:

1. An isolated sample of mammalian major histocompatibility class II heterodimers capable of binding 1.0+/−0.3 mol antigenic peptide per mol heterodimer when said antigenic peptide is added to said sample, wherein said sample is produced by expressing DNA encoding the α and β polypeptides of said major histocompatibility class II heterodimer in an insect cell.

2. The sample of claim 1, wherein said heterodimers are soluble and the α and β polypeptides of each of said heterodimers lack the transmembrane domain normally present on naturally occurring major histocompatibility class II α and β polypeptides.

3. The sample of claim 1 or 2, wherein said heterodimers are human.

4. The sample of claim 1 or 2, wherein said heterodimers are murine.

5. A baculovirus comprising DNA encoding the α polypeptide of a mammalian major histocompatibility class II heterodimer.

6. The baculovirus of claim 5, wherein said α polypeptide lacks the transmembrane domain normally present on naturally occurring α polypeptide.

7. The baculovirus of claim 5, wherein said baculovirus is BV-DRα.

8. The baculovirus of claim 6, wherein said baculovirus is BV-DRαsol.

9. A baculovirus comprising DNA encoding the β polypeptide of a mammalian major histocompatibility class II heterodimer.

10. The baculovirus of claim 9, wherein said β polypeptide lacks the transmembrane domain normally present on naturally occurring β polypeptide.

11. The baculovirus of claim 9, wherein said baculovirus is BV-DRβ.

12. The baculovirus of claim 10, wherein said baculovirus is BV-DRβsol.

13. A method of producing the sample of claim 1, said method comprising expressing the α and β polypeptides of the mammalian major histocompatibility class II heterodimer in insect cells which comprise a baculovirus encoding the alpha polypeptide of a mammalian major histocompatibility class II heterodimer and a baculovirus encoding the beta polypeptide of a mammalian major histocompatibility class II heterodimer, and recovering said heterodimer from said cells or their growth medium.

14. The method of claim 13, wherein said heterodimer is soluble and said cells are coinfected with a baculovirus encoding the alpha polypeptide of a mammalian major histocompatibility class II heterodimer, wherein said alpha polypeptide lacks the transmembrane domain normally present on naturally occurring alpha polypeptide, and a baculovirus encoding the beta polypeptide of a mammalian major histocompatibility class II heterodimer, wherein said beta polypeptide lacks the transmembrane domain normally present on naturally occurring beta polypeptide.

15. A recombinant insect cell which expresses a mammalian major histocompatibility class II heterodimer which lacks bound antigen.

16. The cell of claim 15, wherein said heterodimer is soluble and each of the α and β polypeptides of said heterodimer lacks the transmembrane domain normally present on naturally occurring major histocompatibility class II α and β polypeptides.

17. The cell of claim 15 wherein said cell is coinfected with the a baculovirus encoding the alpha polypeptide of a mammalian major histocompatibility class II heterodimer and a baculovirus encoding the beta polypeptide of a mammalian major histocompatibility class II heterodimer.

18. The cell of claim 16, wherein said cell is coinfected with the a baculovirus encoding the alpha polypeptide of a mammalian major histocompatibility class II heterodimer, wherein said alpha polypeptide lacks the transmembrane domain normally present on naturally occurring alpha polypeptide, and a baculovirus encoding the beta polypeptide of a mammalian major histocompatibility class II heterodimer, wherein said beta polypeptide lacks the transmembrane domain normally present on naturally occurring beta polypeptide.

* * * * *